(12) United States Patent
McKenna et al.

(10) Patent No.: US 7,722,547 B2
(45) Date of Patent: May 25, 2010

(54) DIE SWELL FERTILITY ASSESSMENT FOR HUMANS AND OTHER MAMMALS: APPARATUS AND METHOD

(76) Inventors: Gregory B McKenna, 3024 23rd St., Lubbock, TX (US) 79410; Stephen J. Usala, 7809 Bent Tree, Amarillo, TX (US) 79121; Mark W. Vaughn, 3312 41st St., Lubbock, TX (US) 79409; Jian Wang, 510 That Way, #506, Lake Jackson, TX (US) 77566; Wei Wang, 229 Indiana Ave., D210, Lubbock, TX (US) 79415

( * ) Notice: Subject to any disclaimer, the term of this patent is extended or adjusted under 35 U.S.C. 154(b) by 350 days.

(21) Appl. No.: 11/487,716

(22) Filed: Jul. 17, 2006

(65) Prior Publication Data
US 2008/0027351 A1    Jan. 31, 2008

(51) Int. Cl.
*A61B 10/00*    (2006.01)
(52) U.S. Cl. ..................... 600/551; 73/54.01
(58) Field of Classification Search ........... 600/551
See application file for complete search history.

(56) References Cited

U.S. PATENT DOCUMENTS

| | | | |
|---|---|---|---|
| 3,832,886 A * | 9/1974 | Pliskin ............... | 73/54.13 |
| 3,926,037 A * | 12/1975 | Kopito et al. ............ | 73/54.37 |
| RE30,092 E | 9/1979 | Schuster | |
| 4,237,725 A | 12/1980 | Kopito | |
| 4,454,751 A * | 6/1984 | Matta et al. ............ | 73/54.11 |
| 4,534,362 A | 8/1985 | Schumacher et al. | |
| 4,680,958 A * | 7/1987 | Ruelle et al. ............ | 73/54.14 |
| 4,691,714 A | 9/1987 | Wong | |
| 4,779,627 A * | 10/1988 | Kosasky ............... | 600/551 |
| 5,916,173 A | 6/1999 | Kirsner | |
| 6,110,125 A | 8/2000 | Young | |
| 6,149,591 A | 11/2000 | Henderson | |
| 6,364,844 B1 | 4/2002 | Regas | |
| 6,468,233 B2 | 10/2002 | Kosaky | |
| 6,575,021 B1 | 6/2003 | Kosasky et al. | |
| 6,591,663 B1 | 7/2003 | Murry et al. | |
| 6,793,886 B1 | 9/2004 | Weissmahr | |
| 2003/0144602 A1 | 7/2003 | Jennings | |
| 2004/0167424 A1 | 8/2004 | Mulcaire-Jones | |
| 2004/0171964 A1 | 9/2004 | Heitz | |
| 2005/0042742 A1 | 2/2005 | Marett | |
| 2005/0165326 A1 | 7/2005 | Kirsner | |
| 2005/0171454 A1 | 8/2005 | Catt | |

OTHER PUBLICATIONS

COHU, Inc. Progressive Scan Interline Transfer CCD Camera with Analog Output pp. 1-4 Sep. 1998.*

(Continued)

*Primary Examiner*—Max Hindenburg
*Assistant Examiner*—Renee Danega
(74) *Attorney, Agent, or Firm*—John K. Buche; Buche & Associates, P.C.

(57) ABSTRACT

A method and apparatus for assessing fertility in mammalian females comprising sampling cervical-vaginal fluid, measuring one or more of the sample's viscoelastic properties, and evaluating the measurement to determine fertility. Preferable embodiments of the current invention may utilize measurement of the viscoelastic property of die swell ratio, or other viscoelastic properties of cervical-vaginal fluid.

13 Claims, 6 Drawing Sheets

OTHER PUBLICATIONS

Bigelow. et al., "Mucus observations in the fertile window: a better predictor of conception than timing of intercourse," Hum Reprod. Apr. 2004;19(4):889-92. Epub Feb. 27, 2004.

Billings, "The Ovulation Method, Natural Family Planning," The Liturgical Press, Collegeville, MN, 1994 pp. 16-20.

Brown, et al., "Use of the Home Ovarian Monitor in pregnancy avoidance," Am J Obstet Gynecol. Dec. 1991;165(6 Pt 2):2008-11.

Djerassi, "No political will to seek innovative contraception." Nature. Feb. 17, 2005;433 (7027):683.

Dunson, et al., "Day-specific probabilities of clinical pregnancy based on two studies with imperfect measures of ovulation," Hum Reprod. Jul. 1999;14(7):1835-9.

Ecochard, et al., "Chronological aspects of ultrasonic, hormonal, and other indirect indices of ovulation," BJOG. Aug. 2001;108(8):822-9.

Flynn, et al., "Detection of the fertile phase from changes in cervicovaginal fluid volume," Int J Fertil. 1988;33 Suppl:17-23.

Flynn, et al., "The temporal relationship between vaginal fluid volumes obtained with the Rovumeter vaginal aspirator and the fertile phase of the cycle," Hum Reprod. Feb. 1988;3(2):201-205.

Flynn, et al., "Volumetric self-sampling of cervicovaginal fluid to determine potential fertility: a multicentre pre-effectiveness study of the Rovumeter," Hum Reprod. Aug. 1997;12(8):1826-31.

Freundl, "European multicenter study of natural family planning (1989-1995): efficacy and drop out," Advances in Contraception, 1999;15:69-83.

Freundl, et al., "Estimated maximum failure rates of cycle monitors using daily conception probabilities in the menstrual cycle," Hum Reprod. Dec. 2003;18(12):2628-33.

Gipson, "Mucins of the human endocervix," Front Biosci. Oct. 1, 2001;6:D1245-55.

Gordon and Speroff, "Handbook for Clinical Gynecologic Endocrinology and Infertility," Lippincott Williams and Wilkins, pp. 432 (2002).

Mosher, et al.,"Use of contraception and use of family planning services in the United States: 1982-2002" Adv Data. Dec. 10, 2004;(350):1-36.

Schumacher, et al., "Volume of Vaginal Fluid as a Parameter of the Fertile Period," Abstracts of Papers: Congress of the International Federation for Family Life Promotion, Ottawa, Canada Jun. 29-Jul. 1, 1986, pp. 64-65.

Strauss and Kafrissen, "Waiting for the second coming," Nature. Nov. 2004; 432(7013):43-5.

Usala and Schumacher, "Volumetric self-sampling of cervicovaginal fluid: a new approach to ovulation timing," Fertil Steril. Mar. 1983;39(3):304-9.

Wickstrom, et al., "MUC5B is a major gel-forming, oligomeric mucin from human salivary gland, respiratory tract and endocervix: identification of glycoforms and C-terminal cleavage," Biochem J. Sep. 15, 1998;334 ( Pt 3):685-93.

Wilcox, et al., "Timing of sexual intercourse in relation to ovulation. Effects on the probability of conception, survival of the pregnancy, and sex of the baby," N Engl J Med. Dec. 7, 1995;333(23):1517-21.

Wolf, et al., "Human cervical mucus. I-4. Rheologic characteristics," Fertil Steril. Jan. 1977;28(1):41-6,47-52, 53-8, 163-9,166-9.

Freundl G, Frank-Herrmann P, Raith-Paula E 1998 Natuerliche familienplanung. Gynaekologe 31:398-409.

Carlstedt I, Sheehan JK 1989 Structure and macromolecular properties of cervical mucus glycoproteins. Symp Soc Exp Biol 43:289-316.

Sheehan JK, Howard M, Richardson PS, Longwill T, Thornton DJ 1999 Physical characterization of a low-charge glycoform of MUC5B mucin comprising the gel-phase of an asthmatic respiratory mucous plug. Biochem J 338:507-513.

Raynal BDE, Hardingham TE, Thornton DJ, Sheehan JK 2002 Concentrated solutions of salivary MUC5B mucin do not replicate the gel-forming properties of saliva. Biochem J 362:289-296.

Usala SJ, O'Brien-Usala F, Haciski R, Holt JA, Schumacher GFB 1989 IgG and IgA content of vaginal fluid during the menstrual cycle. J Reprod Med 34:292-294.

Macosko CW 1994 Rheology, principles, measurements, and applications. New York: Wiley VCH; 254-256.

Cloitre M, Hall T, Mata C, Joseph DD 1998 Delayed-die swell and sedimentation of elongated particles in wormlike micellar solutions. Journal Non-Newtonian Fluid Mechanics 79:157-171.

Garcia JE, Jones GS, Wright GL Jr 1981 Prediction of the time of voulation. Fertil Steril 36:308-315.

Joseph DD 1990 Fluid dynamics of viscoelastic liquids. New York: Springer-Verlag; 365-409.

Gipson IK, Moccia R, Spurr-Michaud S, Argueso P, Gargiulo AR, Hill III JA, Offner GD, Keutmann HT 2001 The amount of MUC5B mucin in cervical mucus peaks at midcycle. J Clin Endocrinol Metab 86:594-600.

Argueso P, Spurr-Michaud S, Tisdale A, Gipson IK 2002 Variation in the amount of T antigen and N-acetyllactosamine oligosaccharides in human cervical mucus secretions with the menstrual cycle. J Clin Endocrinol Metab 87:5641-5648.

Raynal BDE, Hardingham TE, Sheehan JK, Thornton DJ 2003 Calcium-dependent protein interactions in MUC5B provide reversible cross-links in salivary mucus. J Biol Chem 31:28703-28710.

Suarez SS, Pacey AA 2006 Sperm transport in the female reproductive tract. Human Reproduction Update 12:23-37.

Behre HM, Kuhlage J, Gassner C, Sonntag B, Schem C, Schneider HPG, Neschlag 2000 Prediction of ovulation by urinary hormone measurements with the home use ClearPlan Fertility Monitor: comparison with transvaginal ultrasound scans and serum hormone measurements. Human Reproduction 15:2478-2482.

\* cited by examiner

DAY   11   12   13   14   15   16

TABLE. ENDOCRINE DATA FOR PATIENT XS3

| DAY OF CYCLE | DIE SWELL RATIO | CVF VOLUME (ML) | URINE LH (0 OR 1) | TEMPERATURE (°F) | SERUM LH (MIU/ML) | SERUM FSH (IIU/ML) | SERUM ESTRADIOL (PG/ML) | SERUM PROGESTERONE (NGML) |
|---|---|---|---|---|---|---|---|---|
| 1 | | | | | | | | |
| 2 | | | | | | | | |
| 3 | | | | | | | | |
| 4 | | | | | | | | |
| 5 | | | | | | | | |
| 6 | | | | | | | | |
| 7 | | | | | | | | |
| 8 | | 0 | | | | | | |
| 9 | | 0 | | 97.5 | | | | |
| 10 | 2.23 | 0.2 | | 97.2 | | | | |
| 11 | 1.96 | 0.1 | | 97.4 | | | | |
| 12 | | 0.3 | | 97.5 | | | | |
| 13 | 2.06 | 1 | 0 | 97.3 | 9.26 | 4.26 | 273 | 0.5 |
| 14 | 1.93 | 0.4 | 1 | 97.7 | 25.1 | 8.42 | 269 | 1.1 |
| 15 | 2.11 | 1.5 | 1 | 97.2 | 7.62 | 5.98 | 76.9 | 1.5 |
| 16 | 2.51 | 0.2 | 0 | 97.6 | 4.73 | 3.95 | 39.5 | 2.5 |
| 17 | | 0.8 | 0 | 97.7 | 4.79 | 4.54 | 50.3 | 5.9 |
| 18 | | 0.3 | | 97.6 | | | | |
| 19 | | 0 | | 97.5 | | | | |
| 20 | | 0 | | 97.7 | 2.2 | 3.09 | 62.4 | 11.7 |
| 21 | | 0 | | 97.3 | 1.26 | 2.64 | 70 | 9.6 |
| 22 | | 0 | | 98.1 | | | | |
| 23 | | | | 98.1 | | | | |
| 24 | | | | 98.1 | | | | |
| 25 | | | | 98.1 | | | | |
| 26 | | | | 98.1 | | | | |
| 27 | | | | 98 | | | | |
| 28 | | | | 97.9 | | | | |

FIG. 6

TABLE 7.1 DIE SWELL AND ENDOCRINE DATA FOR MENSTRUAL CYCLE XS-3

| DAY OF CYCLE | DIE SWELL RATIO (B) | CVF VOLUME (ML) | TEMPERATURE (°C) | URINE LH (0 OR 1) | SERUM LH (MIU/ML) | STRETCHABILITY (MM) |
|---|---|---|---|---|---|---|
| 1 | | | | | | |
| 2 | | | | | | |
| 3 | | | | | | |
| 4 | | | | | | |
| 5 | | | | | | |
| 6 | | | | | | |
| 7 | | 0 | | | | |
| 8 | | 0 | | | | |
| 9(-5) | 2.23 | 0.2 | 36.4 | | | |
| 10(-4) | 1.96 | 0.1 | 36.2 | | | |
| 11(-3) | 2.06 | 0.3 | 36.3 | | | 3 |
| 12(-2) | 1.93 | 1 | 36.4 | | | 3 |
| 13(-1) | 2.11 | 0.4 | 36.3 | 0 | 9.26 | 5 |
| 14(0) | 2.51 | 1.5 | 36.5 | 1 | 25.1 | 10 |
| 15(+1) | | 0.2 | 36.2 | 1 | 7.62 | 22 |
| 16(+2) | | 0.8 | 36.4 | 0 | 4.73 | 45 |
| 17(+3) | | 0.3 | 36.5 | 0 | 4.79 | 12 |
| 18 | | 0 | 36.4 | | | 0 |
| 19 | | 0 | 36.4 | | | |
| 20 | | 0 | 36.5 | | 2.2 | |
| 21 | | 0 | 36.3 | | 1.26 | |
| 22 | | | 36.7 | | | |
| 23 | | | 36.7 | | | |
| 24 | | | 36.7 | | | |
| 25 | | | 36.7 | | | |
| 26 | | | 36.7 | | | |
| 27 | | | 36.7 | | | |
| 28 | | | 36.6 | | | |

DIE SWELL FERTILITY ASSESSMENT FOR HUMANS AND OTHER MAMMALS: APPARATUS AND METHOD

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of Invention

The present application relates generally to medicine and veterinary practice, and, more particularly, methods and apparatus useful for assessing the level of fertility in mammalian females.

2. Background of the Invention

Methods and devices for assessing the level of a woman's, or female mammal's, fertility are important for primarily two reasons: contraception and, conversely, improving the likelihood of conception.

Contraceptive use in the United States is virtually universal among women of reproductive age: 98% of all women who ever had intercourse had used at least one contraceptive method in a 2002 survey (W D Mosher et al., "Use of Contraception and Use of Family Planning Services in the U.S.: 1982-2002", Advance Data, 350:1-36, Dec. 10, 2004, Center for Disease Control (CDC)). The CDC statistics show a high rate of experience with non-chemical and non-barrier methods of contraception. In 2002 the percentage of women 15-44 years of age who have ever had sexual intercourse and who have ever used calendar rhythm was 13.9-16.6%, periodic abstinence/natural family planning was 1.9%-4.7%, and withdrawal was 47.2-59.7% (WD Mosher et al., Advance Data 350:1-36, Dec. 10, 2004, CDC). These data suggest that there is an interest in more "natural" methods of family planning. Fertility experts feel there is a need for "safer, more effective, and more user-friendly contraceptives." (V F Strauss and M. Kafrissen, "Waiting for the second coming", Nature 432: 43-45, 2004).

The other issue of family planning—improving the rate of pregnancy—is not addressed by hormonal or barrier contraception. Sexual intercourse is unlikely to result in conception unless it occurs during the 6-day fertile interval ending on the day of ovulation (D B Dunson et al., Human Reproduction 14:1835-1839, 1999; A J Wilcox et al., NEJM 333:1517-1521, 1995). A problem with fertility is defined as a year of unprotected coitus without conception. This affects 10-15% of couples of reproductive age, and is largely due to improperly timed attempts at conception. Thus, a family planning method that could be used to determine a woman's level of fertility, and thereby increase the probability of pregnancy, would be extremely useful.

Over the past several years there has been much interest in developing methods to predict and detect the time of ovulation and measure the level of fertility throughout the human menstrual cycle. For various health, religious, and philosophic reasons there is a great interest in natural methods of birth control which utilize biologic indicators of fertility to define an interval of sexual abstinence (G Freundl et al., Gynaekologe, 31:398-409, 1998; The European Natural Family Planning Study Groups, Adv Contraception 15:69-83, 1999).

One such method of using biological indicators to assess female fertility, described in U.S. Patent Application #20050171454, employs analysis of a urinary metabolite of estrogen (estrone-3-glucuronide) and luteinizing hormone (LH). One of the primary drawbacks of this method is practicality, as this test is expensive and requires considerable reagents. Additional impracticability, and inaccuracy, may abound in that the levels of urinary estrone-3-glucuronide may be variably connected with the level of fertility depending on the quality of cervical-vaginal secretions. Thus the biological indicator employed in that test may be a derivative, and a step removed, from the primary indicator of cervical-vaginal secretion quality. Other methods of measuring various hormones, such as progesterone, have similar issues of cost, reliability and accuracy.

Many of the other natural methods of family planning in current use (e.g., Billings Method) depend on indicators such as the texture and sensations of cervical mucus and cervical-vaginal secretions to predict the fertile phase of the cycle (J J Billings, The Ovulation Method Manual, Family of Americas Foundation, The Liturgical Press Collegeville, Minn., 1994). These methods are individualistic and subjective, and thus lack quantifiable and objective data for determining the level of a female's fertility.

Some female fertility assessment methods attempt to quantify the various qualities of the cervical mucus, based on the strong correlation between the quality of this fluid and the fertility of a female. Some of the these methods include using a refractomeric device to measure the refractive index of cervical mucus (U.S. Pat. No. 6,149,591), or using acoustic waves to measure the viscosity of cervical mucus (U.S. Pat. No. 4,691,714). Both of these methods again have problems of consistency and accuracy. Additionally, and importantly, both of these methods are impractical for personal use, as it is extremely difficult for women to obtain pure cervical mucus on their own.

The volume of cervical-vaginal secretions has also been employed as a biological indicator of female fertility. As described in U.S. Pat. No. 4,534,362, a Volumetric Vaginal Aspirator has been developed to allow women to take and read the volume of a daily sample of their cervical-vaginal secretions, and observe the timing of a volume peak that occurred approximately simultaneously with the peak in serum estradiol that precedes ovulation—thus predicting fertility. However, tests have shown that this volumetric analysis was able to predict fertility consistently in only a small proportion of women (A M Flynn et al., Human Reproduction 12: 1826-1931). Additionally, many women may not obtain sufficient cervical-vaginal fluid during the fertile period to register a significant enough change indicative of ovulation. Thus, volumetric analysis of cervical-vaginal fluids is also hampered by relatively low sample volumes (~0.2 ml. at volume peak) in some women.

Other devices have attempted to measure the electrical resistance of vaginal fluid. However, again it appears that the measurement phenomena are not always demonstrably reliable.

SUMMARY OF PREFERRED EMBODIMENTS

Accordingly, it is an objective of the present application and various embodiments described herein to provide an improved method and apparatus for assessing female fertility in humans and other mammals.

It is yet another object of the present application and various embodiments described herein to provide an apparatus capable of utilizing the viscoelastic properties of cervical-vaginal fluid to assess a female's level of fertility.

It is a further object of the present application and various embodiments described herein to provide an apparatus capable of utilizing the viscoelastic properties of cervical-vaginal fluid to assess a female's level of fertility, where the type of viscoelastic property analyzed is that of a die swell ratio.

It is another preferable object of the present application and various embodiments described herein to provide a method for assessing female fertility levels, by which a woman could examine herself with little outside assistance.

Other objectives of the application and various embodiments described herein will become apparent to those skilled in the art once the preferred embodiments have been shown and described. These objectives are not to be construed as limitations of applicant's invention, but are merely aimed to suggest some of the many benefits that may be realized by the apparatus and methods of the present application and with its many embodiments.

BRIEF DESCRIPTION OF THE DRAWINGS

The manner in which these objectives and other desirable characteristics can be obtained is explained in the following description and attached drawings in which:

FIG. 7 considers day of cycle, die swell ratio, cervical-vaginal fluid sample volume, basal body temperature (° C.), Urine LH level, Serum LH level, and stretchability (millimeters).

It is to be noted, however, that the appended drawings illustrate only typical embodiments of this invention and are therefore not to be considered limiting of its scope, for the invention may admit to other equally effective embodiments that will be appreciated by those reasonably skilled in the relevant arts. Also, drawings are not necessarily made to scale but are representative.

DETAILED DESCRIPTION OF PREFERRED EMBODIMENTS

Figure 1:
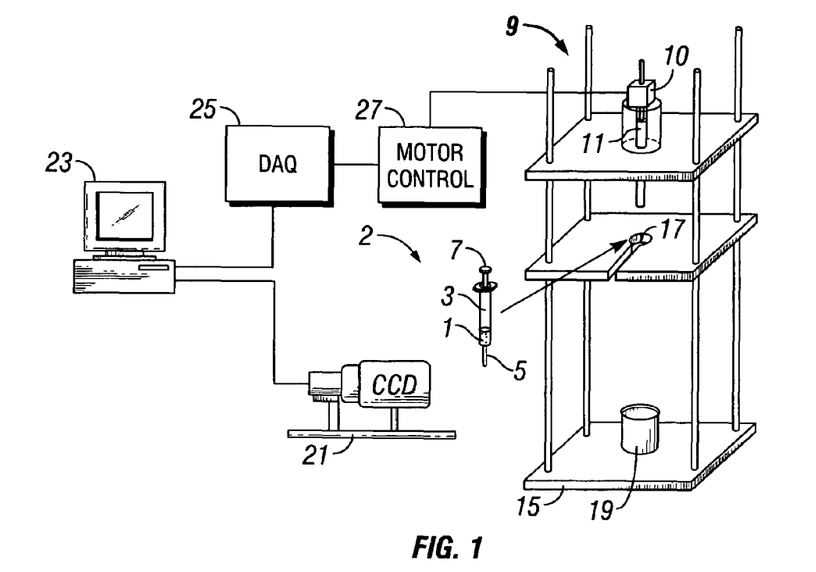
FIG. 1 is a perspective view of a preferable die swell fertility apparatus.

FIG. 1 is a perspective view of a preferable fertility assessment apparatus, for use in an analysis of viscoelastic properties of cervical-vaginal fluid, including to assess fertility levels. Viscoelastic properties of cervical-vaginal fluid fluctuate in a measurable and meaningful way throughout the menstrual cycle, and likely correspond to sperm's survival and/or motility rates, and which properties correlate with various hormonal changes effecting fertility. Fertility, as referred to in this disclosure, is a term speaking to the tendency or capacity of an individual to become or not become pregnant. Fertility may also relate to the time(s) at which the cervical-vaginal fluid donor is most likely to become pregnant. By assessing fertility, this disclosure is referring to a prediction of this time, whether the time the donor is most likely to become pregnant is already past, current, or at some point in the future. The analysis of the measurement can be either of the absolute value of the measurement or by comparing the change between the current and past measurements. The viscoelastic properties of the cervical-vaginal fluid will decrease or increase as ovulation approaches depending on the viscoelastic property measured. This should be observable for several days prior to ovulation. After ovulation, the viscoelastic properties of the cervical-vaginal fluid will increase or decrease respectively depending on the viscoelastic property. However, this process is not limited to comparison of a series of measurements, as the absolute value of these measurements alone may be an indication of fertility.

The preferable embodiment depicted in FIG. 1 is an apparatus useful for analyzing the viscoelastic property of die swell ratio of a sample of cervical-vaginal fluid 1. Cervical mucus is a hydro-gel-like substance with viscoelastic properties; these properties are mainly due to the large glycoprotein MUC5B, which is a gel-forming, oligomeric mucin. The hydration content and viscoelastic characteristics of MUC5B and cervical mucus tend to change as a function of phase of the menstrual cycle. Cervical-vaginal fluid, which contains cervical mucus, retains viscoelastic properties, which are a function of phase of the menstrual cycle and can be measured with preferred embodiments described herein. The Die swell or extrudate swell is related to a substance's elasticity. The term die swell is used to describe the expansion of a polymer solution or fluid through a die 5 (or capillary tube or nozzle) and can be quantified as a die swell ratio defined as: $B = D/(2R)$, where B is the die swell ratio, D is the diameter of the expanding fluid when extruded through a die 5, and 2R is the inner diameter of the die 5. Cervical-vaginal fluid is also preferably described as a non-Newtonian fluid susceptible to analysis by die swell. The normal force present in the die swell process is proportional to the elastic modulus, which in turn is proportional to the die swell ratio to the third power ($B^3$). Thus, the die swell ratio is a preferable parameter to measure the viscoelasticity of cervical-vaginal fluid and is related to phase of the menstrual cycle. Die swell ratio, B, is typically defined as the maximum diameter of the extruded fluid ($D_{ex}$) divided by the inner diameter of the die (2R) and usually increases as shear rate increases. The die swell ratio is also affected by the die's length to radius ratio, L/R. When $L/R > 16$, the flow velocity gradient near the inlet of the die may preferably be ignored and die swell is only due to the first normal stress difference. When $L/R > 40$, the die swell ratio is preferably regarded as independent of die geometry. These features have been incorporated into the preferred embodiment detailed below, though they are not essential. Further, the method and apparatus disclosed in the present application may also use the die swell width as a measurement, if the same die 5 is used for all measurements. In that instance, the percentage change in the width is equivalent to the change in the die swell ratio. For two measurements of die swell diameter $D_1$ and $D_2$, $(D_1/D_2)=(D_1/2R)/(D_2/2R)$ where R is the inner radius of the die 5 as described above. Further, an arbitrary number could also be used for R in this situation and still be a viable method. However, it must be noted that other methods and embodiments are contemplated for measuring any other viscoelastic properties of cervical-vaginal fluid 1 apart from the die swell ratio.

Basic preferable components shown in the assembly FIG. 1 comprise an extrusion apparatus 2, a motor apparatus 9, a mounting apparatus 15, a camera 21, and a computer 23. The extrusion apparatus 2 preferably serves as the die 5, but it is contemplated that any other controllable method of fluid extrusion could serve this function with similar results. As shown in FIG. 1, a preferable embodiment of the extrusion apparatus resembles a typical syringe and may comprise an extrusion body 3, die 5, and extrusion plunger 7. As noted above, the inner diameter of the die 5 may, but need not, be known for proper die swell analysis.

Figure 2A:
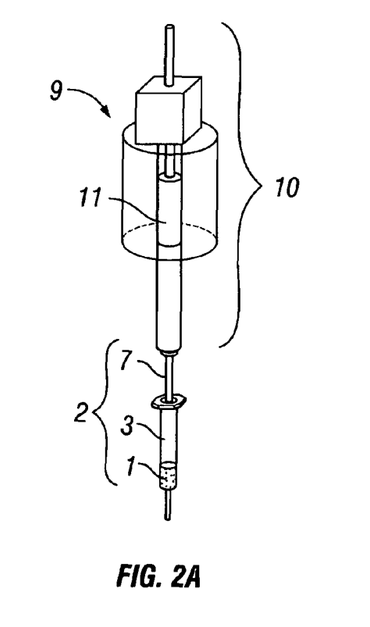
FIGS. 2A, 2B and 2C comprise a perspective view of the motor apparatus and extrusion apparatus of a preferable embodiment of the present application, shown through three stages of operation.
Figure 2B:
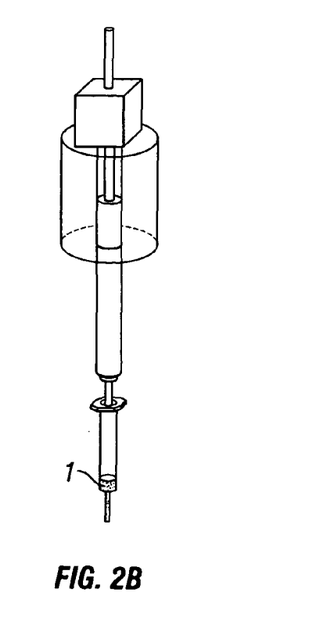
Figure 2C:
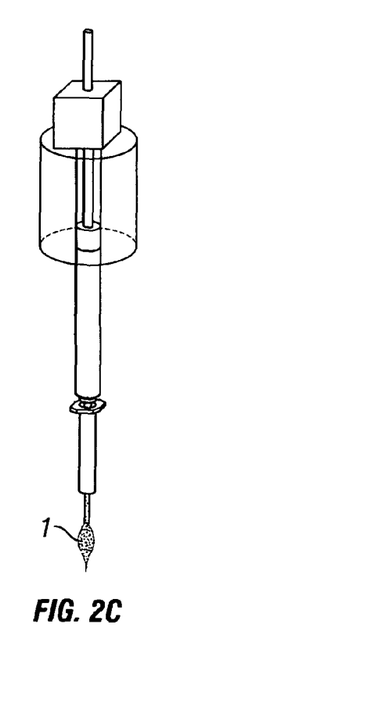

As depicted in FIG. 1, a preferable motor apparatus 9 may be comprised of a motor 10 and a piston 11. Through its interaction with the computer 23 and motor control 27, a motor apparatus 9 preferably serves to control the rate of extrusion through the extrusion apparatus 2. Thus, one skilled in the art could envision any number of methods for controlling the rate of extrusion, including but not limited to vacuum tubing, hydraulic, or other mechanical means. In this instance, the moving velocity of the plunger 7, which is rigidly affixed to the piston 11, is regulated by a motor control 27 (or digital variable resistor) connected to the motor 10 (linear stepper preferred). In calibrating an extrusion apparatus 2, a user may preferably consider that shear flow rate of a viscous fluid on the inner wall of a capillary tube is called wall shear rate and is typically calculated by $(4Q)/((pi)(R^3))$, where Q is volumetric flow rate and R is the inner radius of the capillary tube. Volumetric flow rate may be obtained by the product of the inner area of a syringe and the moving velocity of the plunger. FIGS. 2A, 2B, and 2C show the details of one preferable syringe and needle, which serves as the die. A preferred 1 ml or lesser volume disposable syringe may hold the cervical-vaginal fluid sample, although other sizes may work. Also preferable is a 21-gauge blunt tip needle (OD=0.032 in, ID=0.02 in, L/R=50), or other size may be attached to the syringe. The moving velocity of the piston 11, which should preferably equal the moving velocity of the plunger 7, is preferably regulated by a digital variable resistor connected to a motor 10. The velocity of the piston 11 may then preferably be calibrated by an optical method: let the piston 11 move a short distance, measure the initial and end height difference at the lower edge of the piston 11 through a cathetometer along with the elapsed time, and the true moving velocity of the piston 11 at a given resistor value is obtained. The corresponding wall shear rate is then obtainable. As wall shear rate increases, the die swell ratio increases but the flow time of the cervical-vaginal fluid shortens. The optimal wall shear rate is the greatest die swell ratio where the steady flow region can be determined, though non-optimum shear rates can be used.

FIG. 1 also displays a preferable arrangement of the mounting apparatus 15. Although other arrangements are contemplated, in this embodiment, the mounting apparatus 15 is comprised of a three-tiered rack system for accommodating the motor apparatus 9, extrusion apparatus 2, and collection receptacle 19. In this embodiment, the extrusion apparatus 2 is preferably secured in the extrusion device mounting mechanism 17 at a position adjacent to, and in contact with, the distal portion of piston 11 of the motor apparatus 9, and substantially perpendicular to the camera 21 in the camera's 21 field of vision. In this preferred embodiment the extrusion apparatus mounting mechanism 17 is merely an aperture through which the extrusion device 2 may be securely fixed, but one skilled in the art may envision any number of ways of removably affixing the extrusion device 2 to the mounting apparatus 15. The piston 11 rests upon the plunger 7 and, upon activation by the stepper motor 10, may cause extrusion of the cervical-vaginal fluid 1. The collection receptacle 19 rests on the bottom tier of the mounting apparatus 15 and serves to catch the fluid 1 as it is extruded from the die 5. The collection receptacle 15 may be comprised of countless shapes and materials capable of performing this function.

Also depicted in FIG. 1 is a preferred interaction of the camera 21, computer 23, data acquisition device (DAQ) 25, and motor control 27. The computer 23 serves to view and analyze images captured by the camera 21, and to synchronize the initiation of the motor apparatus 9. In this embodiment, the stepper motor 10 is directly controlled by a motor control 27 (or chopper drive), which itself is optionally controlled by the computer 23 through a preferable DAQ board 25. The motor control 27 is preferably any means useful to convert or harness electronic information acquired or received from the DAQ or computer into commands or information usable for directing or communicating with or controlling operation of the stepper motor 10. These preferable components may combine to control the start, speed, regulation, and duration of the stepper motor's 10 operation—and one skilled in the art will be able to envision numerous ways of performing this function. The camera 21 is preferably capable of taking high quality video at a high level of zoom, such that the video imagery of the fluid 1 expulsion is of analytical quality, and capable of being transferred to the computer 23. This camera 21 may be, but is not limited to, a high resolution CCD video camera equipped with a high magnification close zoom lens capable of recording video at the speed of a preferable rate of 30 frames per second (fps). Other speeds or frames per unit of time may be desirable.

As depicted in FIG. 1, a preferable embodiment of a method employing a die swell fertility assessment apparatus operates as follows. Cervical-vaginal fluid 1 is typically collected from the female subject's upper vagina or posterior fornix region, and placed in the extrusion apparatus 2. This fluid may be collected by the woman or technician through use of any number of extraction methods including but not limited to: swabbing, a common dull-tipped syringe, or something akin to the Volumetric Vaginal Aspirator of U.S. Pat. No. 4,534,362. The volume of cervical-vaginal fluid withdrawn for the testing may be approximately 0.2-0.5 ml, but the apparatus and methods described herein are not intended to be limited by this volume range. As an example, a ½ inch long 21-gauge blunt tip needle may preferably serve as the die 5 and is affixed to the distal end of the extrusion apparatus 2. The extrusion apparatus 2 is then preferably firmly mounted into the extrusion apparatus mounting mechanism 17 in a position spanning the region from the bottom of the piston 13 to the field of vision of the camera 21. The user then may preferably initiate function of the device via the computer 23 interface, causing the DAQ 25 and motor control 27 to signal the stepper motor 10 to begin the extrusion process.

FIGS. 2A, 2B, and 2C depict a typical progression of the motor apparatus 10 and expulsion apparatus 2 upon initiation of the extrusion process. The activated stepper motor 10 is rigidly affixed to the piston 11 and causes it to move, at a regulated speed and distance, downward (FIG. 2B). As the piston 11 is in direct contact with the plunger 7 of the extrusion apparatus 2, the downward movement of the piston 11 causes proportionate downward movement of the plunger 7. The downward movement of the plunger 7 causes pressure in the extrusion body 3, which results in the cervical-vaginal fluid 1 being extruded from the die 5 (FIG. 2C).

Figure 3:
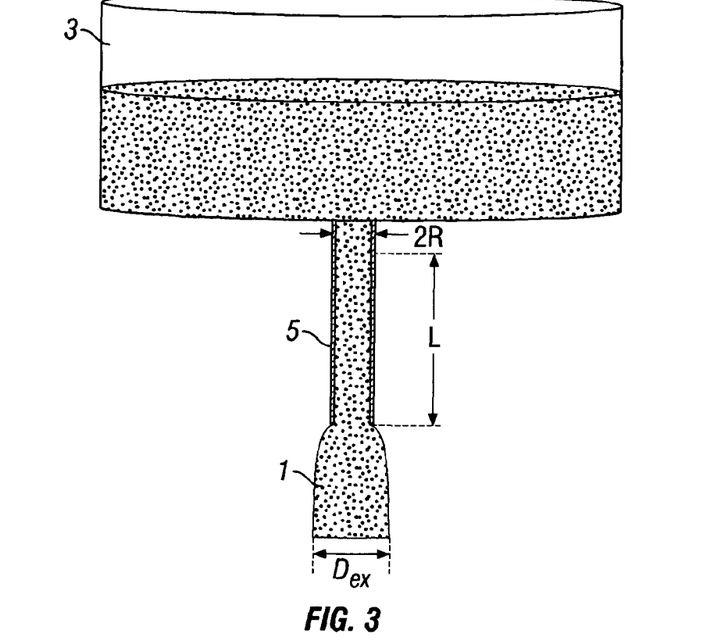
FIG. 3 is an enlarged front view of the extrusion apparatus of a preferable embodiment of the present application.

FIG. 3 depicts an enlarged view of the cervical-vaginal fluid 1 exiting the extrusion body 3 and the die 5. Important measurements of note that may be made include 2R which indicates the inner diameter of the die 5, L that indicates the length of die 5, and $D_{ex}$ which indicates the maximum diameter of the cervical-vaginal fluid swell.

Simultaneously with expulsion of the cervical-vaginal fluid 1 through the die 5, the camera 21 records the flow of fluid 1 for analysis through direct inspection of images or through image processing. In the case of analysis using inspection, dozens of frames are typically viewed and the steady flow region is identified. The steady flow region is preferably defined as the extrusion depicted in a camera frame where the maximum diameter of cervical-vaginal fluid swell ($D_{ex}$) is at equilibrium. One frame within this steady flow region is selected by inspection on the computer 23 and converted into an image for further analysis. From analysis of this frame the die swell ratio is obtained by the ratio of $D_{ex}$ (the diameter of the maximum swell or flow) to 2R (the inner diameter of the needle).

Figure 4:
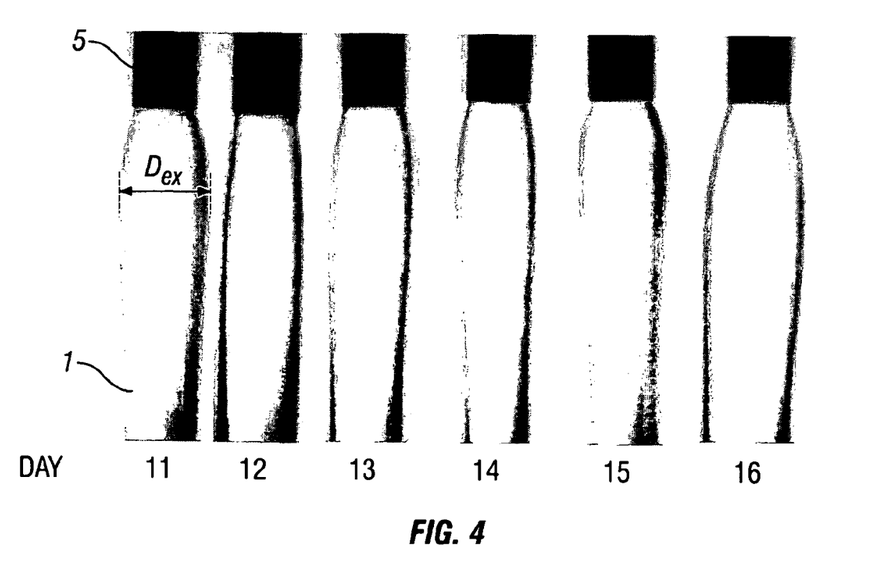
FIG. 4 depicts the die swell images of samples of cervical-vaginal fluid for days 11, 12, 13, 14, 15, and 16. The day of putative ovulation was Day 14.

FIG. 4 depicts video data from the steady flow region captured by the camera 21 and displayed on the computer 23. These images are of the die swells created using cervical-vaginal fluid samples 1 from a human patient (XS3) for days (from left to right in FIG. 4) 11, 12, 13, 14, 15, and 16 of her menstrual cycle. Day 14 is the day of serum luteinizing hormone (LH) peak, or the day of putative ovulation. Days 11, 12, 13, 14, 15, and 16 correspond to days −3, −2, −1, 0, +1, +2, respectively, where day 0 is the day of ovulation. FIG. 4 shows the die swell ratio as a preferable parameter used for fertility and infertility signals and is readily obtainable from the die swell fertility assessment apparatus. The die swell ratio (B) for cervical-vaginal fluid samples from a patient (XS3) are shown. Also shown in FIG. 4 is the measurement $D_{ex}$ which corresponds to the maximum diameter of the cervical-vaginal fluid 1 die swell. This measurement may be taken by hand utilizing a ruler on a computer 23 printout, or one skilled in the art may envision computer software or other means to automate the measurement process. The video frames depicted were chosen from dozens of frames to select the steady flow region for each cervical-vaginal fluid sample; that is, the frames where the maximum diameter of cervical-vaginal fluid swell ($D_{ex}$) is at a preferable equilibrium. It can be observed from the pictures that even without precise measurement of $D_{ex}$ and die swell ratio, significant differences in the maximum diameter of flow for the cervical-vaginal fluid samples may be visualized. The less fertile days 11 (−3), 15 (+1), and 16 (+2) show greater die swell (extrudate diameters) consistent with a greater storage modulus G', which is the preferred term to describe a storage or elastic modulus, and which term reflects the ability of materials to store energy. Cervical mucus, which contains the heavily-glycosylated MUC5B protein with intermolecular disulphide bonding is a protein that shows viscoelastic behavior. Previous researchers have employed a microrheometer to determine the values of G' as a function of frequency for pure cervical mucus throughout the menstrual cycle and demonstrated a minimum in G' with the estrogen peak and near the time of ovulation, and that linear viscoelastic properties of cervical mucus change with the phase of the menstrual cycle. However, the preferred embodiment described herein contemplates measurement of one nonlinear viscoelastic property, namely a die-swell ratio, of cervical-vaginal fluid, which is useful in advanced fertility detection. Die-swell or extrudate swell has been related to a material's elasticity, though it is a non-linear viscoelastic manifestation of this elasticity. It is generally used in investigations of polymer rheology, though is not limited to this use. The term die swell is preferably used to describe the expansion of a polymer solution or fluid through a capillary tube (die or nozzle) and can be quantified as a die swell ratio defined as: B=D/(2R), where B is the die swell ratio, D is the diameter of the expanding polymer solution when extruded through a die, and 2R is the inner diameter of the capillary or die. Die swell ratio typically increases as shear rate increases and is affected by the die's length to radius ratio. Die swell ratio (B) has been found empirically to increase as the elastic or storage modulus G'; B is proportional to $(G')^{1/3}$. In a disclosed preferred embodiment, the time-in-cycle changes in the die swell behavior of vaginal-cervical fluid are employed for a method for fertility monitoring in humans and other mammals. The die swell ratio, B, is preferably calculated for each cervical-vaginal fluid sample from days 11, 12, 13, 14, 15, and 16 of the menstrual cycle of patient XS3. The die swell ratio, B, is calculated from the maximum flow diameter, $D_{ex}$, divided by the inner diameter of the needle. Die swell ratio B is plotted as a function of day of cycle (11 (−3), 12 (−2), 13 (−1), 14 (0), 15 (+1), and 16 (+2)). Fertile days −2, −1, and 0 show cervical-vaginal fluid with B values less than 2.1. Relatively infertile day −3 demonstrated a B value of ~2.23. After ovulation, which occurred on day 14, the B value rose precipitously. By day +2 with progesterone value of 2.5 ng/ml, the B value was ~2.5. Of interest and significance, even though the cervical-vaginal fluid volume on day +2 (day 16) was high at 0.8 ml, which was misleading in terms of indicating fertility, the B value was quite high correctly indicating ovulation had already occurred and that the patient was clearly in the infertile phase. The B value is therefore highly beneficial to indicating the fertile and infertile phases. The die swell ratio B is a reliable parameter that can track the time of cycle: the characteristic function is a declining B value as fertility increases, a minimum B value at the time of maximal fertility and near the time of ovulation, and a rapidly increasing B value after ovulation and with the start of the luteal phase. The phasing of the die swell ratio B and/or the absolute value of the die swell ratio B can be used as an indicator of fertility in the follicular phase and the transition to the absolutely infertile luteal phase.

Figure 5:
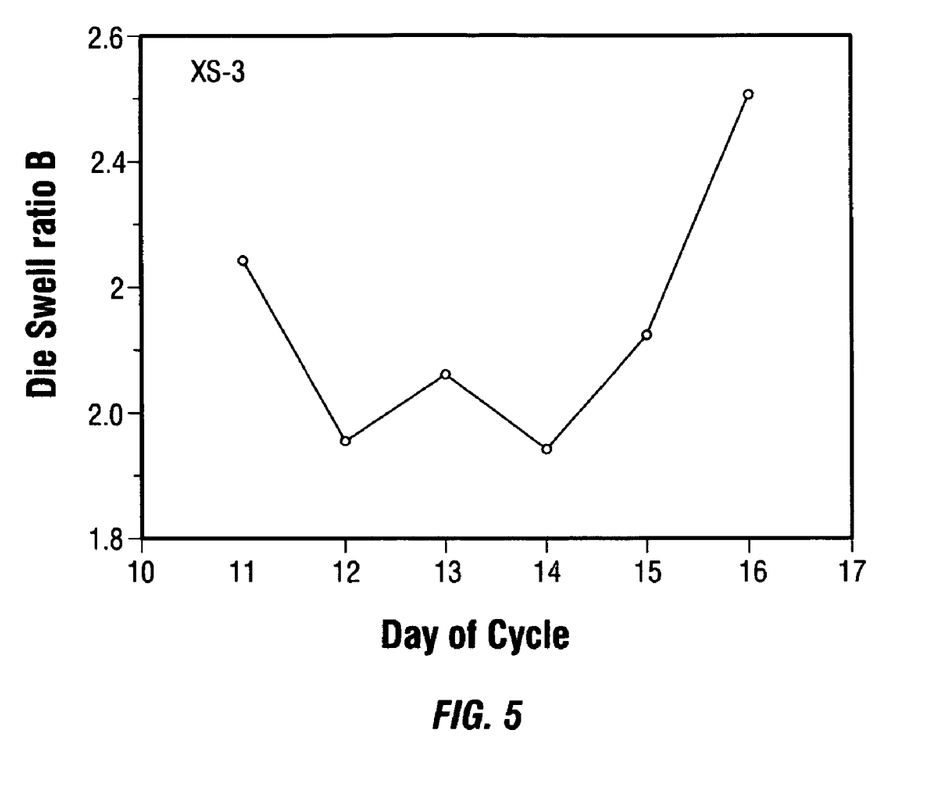
FIG. 5 depicts a line graph of plotted die swell ratios as a function of a day in a woman's fertility cycle.

FIG. 5 displays the die swell ratio as a function of the day of cycle plotted on a graph. The die swell ratio diminishes as ovulation is approached, reaches a minimum on the day of the serum LH peak (day of presumptive ovulation) and rapidly rises after ovulation. The level of fertility correlates with the reduction in the die swell ratio. The level of fertility may be monitored by an absolute level of die swell ratio, by the rate of change of die swell ratio, or by the spectrum of the rate of change of die swell ratio. A combination of any of these data may also be employed. The start of the infertile phase is signaled by the increase in die swell ratio. Family planning decisions regarding the timing of sexual intercourse may then be based upon these die swell data. Similarly, timing of breeding or artificial insemination in mammals may then be based upon these die swell data.

Figure 6:
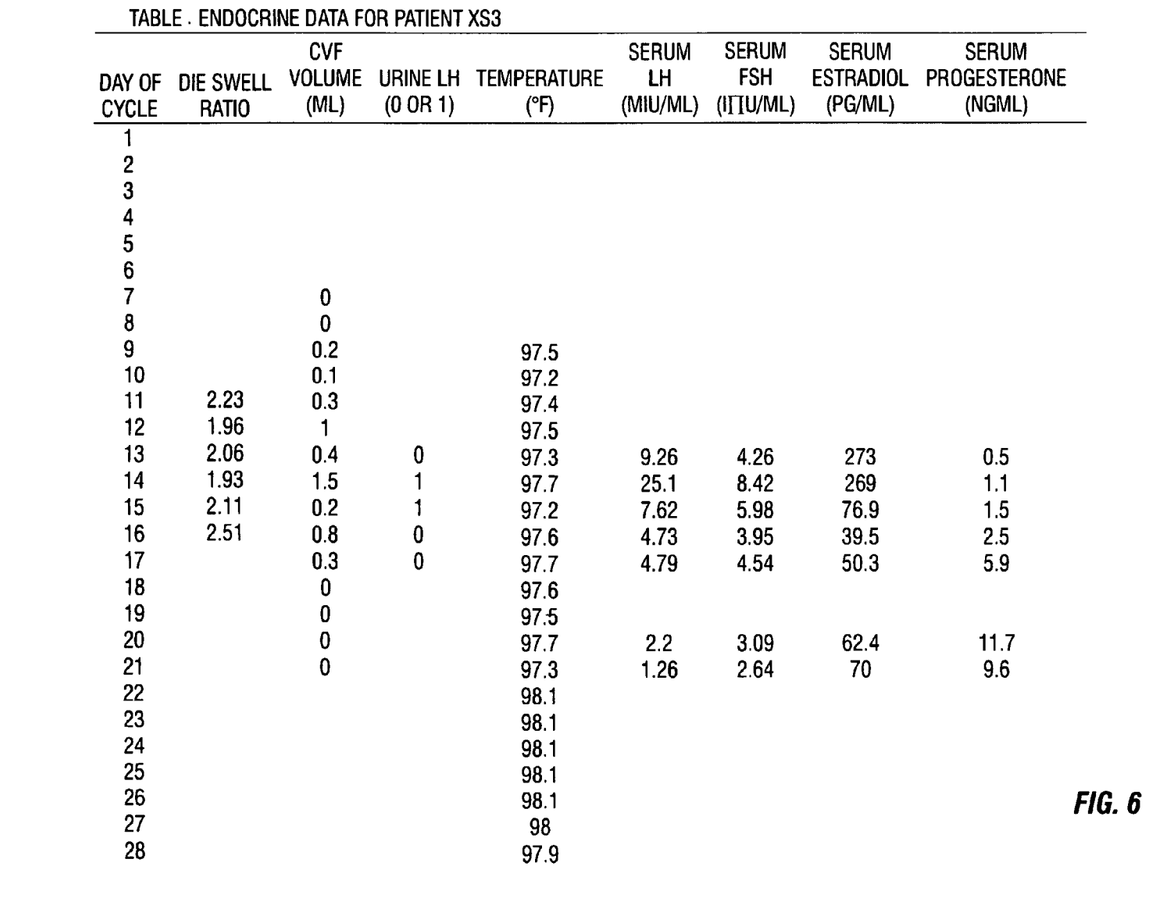
FIGS. 6 and 7 are tables that represent data from a case study for the menstrual cycle of a patient (XS3). Included as data in FIG. 6 as a function of day of cycle are: cervical-vaginal fluid sample volume, urine LH (luteinizing hormone) level, basal body temperature, serum LH, serum follicle stimulating hormone (FSH), serum estradiol, and serum progesterone levels. Day of putative ovulation (serum LH peak) is day 14.
Figure 7:
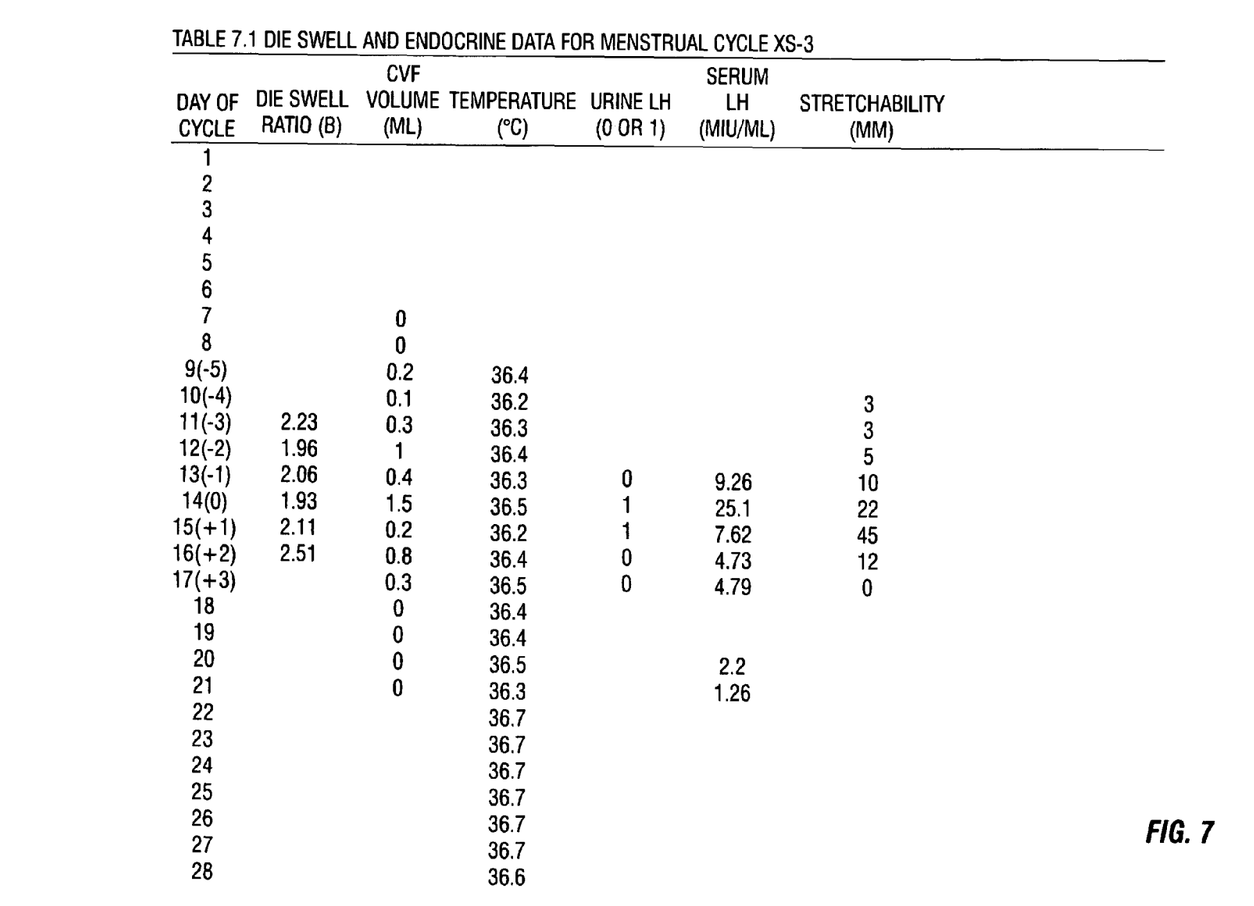
Figure 8:
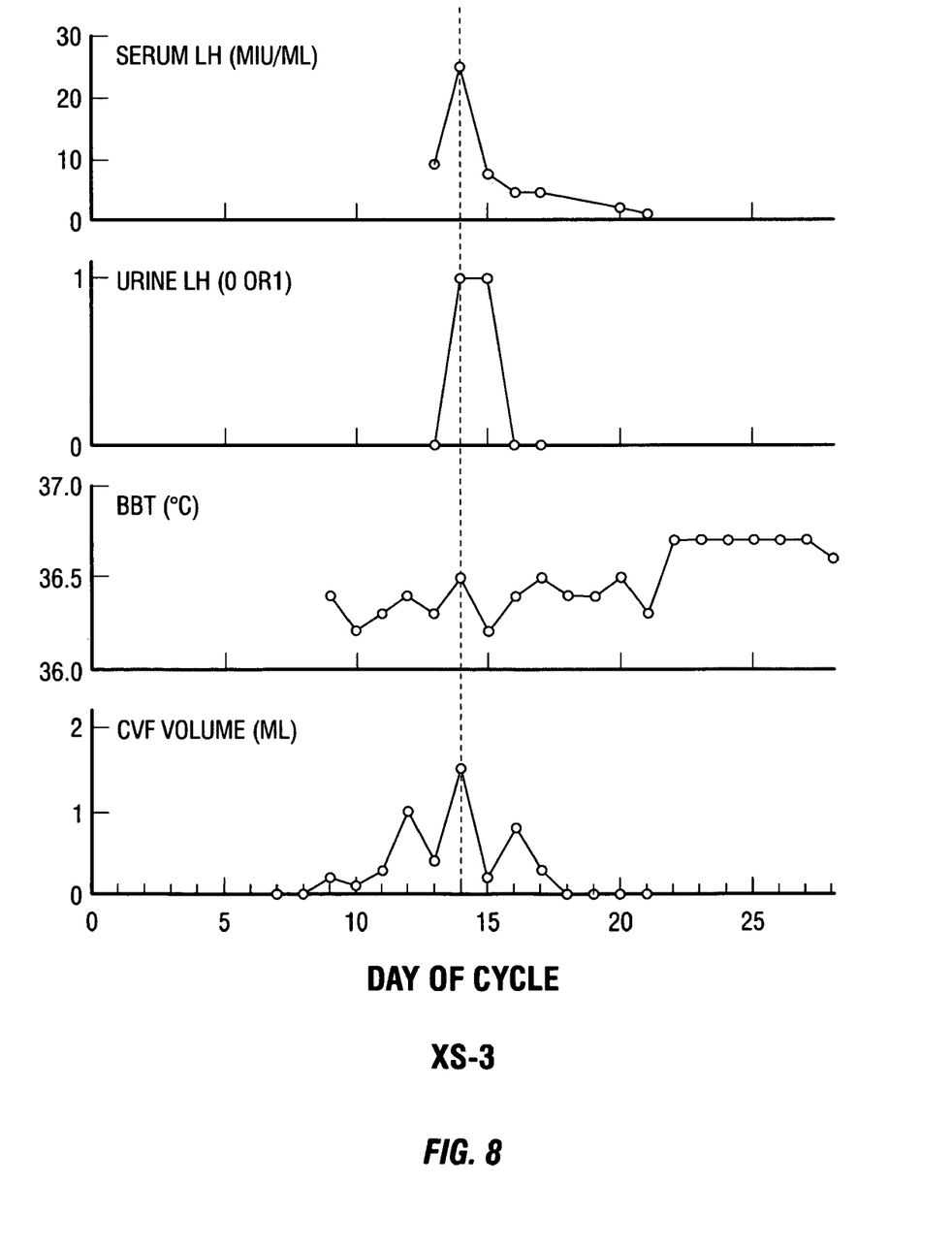
FIG. 8 is a graphical depiction of various physiological measurements from the case study of the menstrual cycle of a patient (XS3).

FIG. 6 represents one sample of data obtained from a study employing some of the preferred embodiments described herein. The endocrine data for patient cycle XS3 are detailed. A comparison is made of endocrine data with the die swell ratio B, which data relate to an improvement in fertility assessment and/or ovulation detection. The day of ovulation occurred on day 14, the day of the serum luteinizing hormone (LH) peak. Urinary LH was positive for two days, day 14 and day 15; recent data have suggested that the initial rise in urinary LH is a better index of ovulation, which correlates here with the serum LH peak (R. Ecochard et al., British Journal of Obstetrics and Gynecology, 108:822-829, 2001). A urinary LH kit would not have provided as good an indicator of the fertile phase as the die swell ratio B measurements; the urinary LH signaled only days 14 and 15 as fertile. Day 15 is post-ovulatory and relatively infertile; die swell ratio B indicated highly fertile days of 12, 13, and 14. The basal body temperature, which is a common natural family planning method to signal the absolutely infertile luteal phase was difficult to interpret in this cycle, and indicated clear luteal phase only late on day 22 and after. The cervical-vaginal fluid sample volume was sometimes relatively low during the fertile phase (volume=0.4 on day 13) and relatively high during the clearly infertile post-ovulatory phase (volume=0.8 on day 17). The die swell ratio B was independent of cervical-vaginal fluid volume and only dependent upon the elastic modulus of the fluid, which in turn is dependent upon the phase of the menstrual cycle and level of fertility.

Preferable embodiments disclosed herein include a fertility assessment apparatus comprising: an extrusion apparatus through which fluid may be extruded; said extrusion apparatus being removably affixed to a motor apparatus which, upon activation causes a fluid to be extruded from the extrusion apparatus, and, a device for capturing the image of the fluid being extruded. Further disclosed is a fertility assessment apparatus further comprising an extrusion apparatus that is a syringe. Further disclosed is a fertility assessment apparatus further comprising a mounting apparatus that maintains extrusion apparatus and motor apparatus in proper relation to one another. Further disclosed is a fertility assessment apparatus further comprising a motor apparatus consisting of a stepper motor and piston. Further disclosed is a fertility assessment apparatus further comprising a computer that controls the initiation of fluid extrusion and image acquisition. Further disclosed is a fertility assessment apparatus further comprising a computer, which controls the initiation of fluid extrusion and image acquisition by the use of a data acquisition board and motor control. Further disclosed is a method of assessing fertility in mammalian females comprising: measuring one or more viscoelastic properties of a collected cervical-vaginal fluid sample; and, analyzing said measurement to determine fertility. Further disclosed is a method wherein said analysis is of the absolute value of the measurement to determine fertility levels. Further disclosed is a method wherein said analysis is of the change over time between the current and prior measurements to determine fertility levels. Further disclosed is a method wherein the period between measurements is daily. Further disclosed is a method wherein a property measured is a die swell ratio. Further disclosed is a method wherein the measurement is obtained by extruding cervical-vaginal fluid through a die and capturing the image of said extrusion by camera. Further disclosed is a method of utilizing a fertility assessment apparatus comprising an extrusion apparatus through which fluid may be extruded, said extrusion apparatus being removably affixed or adjacent to a motor apparatus which, upon activation causes a fluid to be extruded from the extrusion apparatus, and a device for capturing the image of the fluid being extruded. Further disclosed is a method utilizing a mounting apparatus that maintains the extrusion apparatus and motor apparatus in proper relation to one another. Further disclosed is a method of using a computer that controls the initiation of fluid extrusion and image acquisition. Further disclosed is a method of a computer that controls the initiation of fluid extrusion and image acquisition by the use of a data acquisition board and motor control. Disclosed is A fertility assessment apparatus comprising: An extrusion apparatus through which fluid is forced; a force generating means removably attached to said to extrusion apparatus and operably configured to cause extrusion of said fluid from said extrusion apparatus; and, a camera for recording images of extrusion of said fluid. Further disclosed is a fertility assessment apparatus wherein said force generating means is a motor apparatus. Further disclosed is a fertility assessment apparatus wherein said extrusion apparatus is a syringe. Further disclosed is a fertility assessment apparatus wherein said extrusion apparatus is oriented to permit extrusion of said fluid in a downward direction. Further disclosed is a fertility assessment apparatus further comprising a computer, said computer electronically coupled to said camera. Further disclosed is a fertility assessment apparatus further comprising a computer electronically coupled to said force generating means, whereby said computer may communicate with said force generating means. Further disclosed is a fertility assessment apparatus wherein said computer is electronically coupled to a data acquisition device and motor control that communicate data between said force generating means and computer.

We claim:

1. A method of assessing fertility in mammalian females comprising:
    (a) measuring one or more viscoelastic properties of a collected cervical vaginal fluid sample; and,
    (b) analyzing said measurement to determine fertility, said viscoelastic properties being chosen from a selection consisting essentially of either die swell, delayed die swell, or capillary flow analysis.

2. The method of claim 1 wherein said analysis is of the absolute value of the measurement to determine fertility levels.

3. The method of claim 1 wherein said analysis is of the change over time between the current and prior measurements to determine fertility levels.

4. The method of claim 3 wherein the time between measurements is daily.

5. The method of claim 1 wherein a property measured is a die swell ratio, and said property is measured with the aid of one or more flowgrams.

6. The method of claim 1 wherein the measurement is obtained by extruding cervical-vaginal fluid through a die and capturing the image of said extrusion by camera, said camera capable of recording at a speed of at least 30 frames per second.

7. The method of claim 1, wherein said cervical-vaginal fluid sample is collected by female herself, whereby said analysis is used to control fertility.

8. The method of claim 1 utilizing a fertility assessment apparatus comprising an extrusion apparatus through which fluid may be extruded, said extrusion apparatus being removably affixed or adjacent to a motor apparatus which, upon activation causes a fluid to be extruded from the extrusion apparatus, and a device for capturing the image of the fluid being extruded, said device comprising a camera capable of recording at a speed of at least 30 frames per second and featuring a high-magnification lens.

9. The method of claim 8 further utilizing an extrusion apparatus comprising a syringe.

10. The method of claim 8 further utilizing a mounting apparatus that maintains the extrusion apparatus and motor apparatus in proper relation to one another.

11. The method of claim 8 further utilizing a motor apparatus consisting of a stepper motor and piston.

12. The method of claim 8 further utilizing a computer that controls the initiation of fluid extrusion and image acquisition.

13. The method of claim 8 further utilizing a computer that controls the initiation of fluid extrusion and image acquisition by the use of a data acquisition board and motor control.

* * * * *